(12) United States Patent
Davey (10) Patent No.: US 6,491,620 B1
(45) Date of Patent: Dec. 10, 2002

(54) SHAM FOR TRANSCRANIAL MAGNETIC STIMULATOR

(75) Inventor: Kent R. Davey, New Smyrna Beach, FL (US)

(73) Assignee: Neotonus, Inc., Marietta, GA (US)

( * ) Notice: Subject to any disclaimer, the term of this patent is extended or adjusted under 35 U.S.C. 154(b) by 0 days.

(21) Appl. No.: 09/518,596

(22) Filed: Mar. 3, 2000

Related U.S. Application Data (63) Continuation-in-part of application No. 09/501,457, filed on Feb. 10, 2000, now abandoned, and a continuation-in-part of application No. 09/001,782, filed on Dec. 31, 1997, now Pat. No. 6,086,525, which is a continuation-in-part of application No. 08/345,572, filed on Nov. 28, 1994, now Pat. No. 5,725,471.

(51) Int. Cl.[7] .............................................. A61B 17/52
(52) U.S. Cl. ............................................. 600/9; 600/15
(58) Field of Search ....................... 600/9–15

(56) References Cited

U.S. PATENT DOCUMENTS

| 4,940,453 A | | 7/1990 | Cadwell | |
|---|---|---|---|---|
| 5,116,304 A | | 5/1992 | Cadwell | |
| 5,197,940 A | * | 3/1993 | Sievert et al. | 600/9 |
| 5,441,495 A | | 8/1995 | Liboff et al. | |
| 6,203,486 B1 | * | 3/2001 | Miller et al. | 600/9 |

FOREIGN PATENT DOCUMENTS

RU 2008946 3/1994

OTHER PUBLICATIONS

K. Davey and Lanbo Luo, Toward Functional Magnetic Stimulation Theory (FMS) and Experiment, submitted to IEEE Transactions on Biomedical Engineering (submitted in Jul. 1993).

* cited by examiner

*Primary Examiner*—John P. Lacyk
(74) *Attorney, Agent, or Firm*—Levisohn, Lerner, Berger & Langsam, LLP (57) ABSTRACT

The invention relates to an apparatus for simulating the look, sounds and vibrations of a genuine transcranial magnetic stimulator ("TMS"), while keeping the induced current reaching the patient low. The invention involves a sham TMS which presents the appearance of a genuine TMS, but which, in fact, does not operate as would a genuine TMS, because the induced current provided to the patient is captured by an aluminum shroud overlaying the end faces of the core of the TMS. The sham TMS may be used to provide a control in a medical study seeking to compare the results obtained by a genuine TMS with a sham TMS. Because the sham TMS appears to be genuine to the operator of the sham TMS and to the patient, the results of the medical study are not influenced by the knowledge of the operator and/or patient as to whether the TMS device is genuine or sham. The invention, in its preferred embodiment, comprises a thin sheet of continuous aluminum which extends over the center and beyond the end faces of an open core, magnetic nerve stimulator.

15 Claims, 8 Drawing Sheets

SHAM FOR TRANSCRANIAL MAGNETIC STIMULATOR

RELATED APPLICATIONS

This application claims the priority of the U.S. patent application Ser. No. 08/345,572, filed Nov. 28, 1994, which issued as U.S. Pat. No. 5,725,471; the U.S. Provisional Application Serial No. 60/023,421, filed Aug. 15, 1996; the PCT International Application No. PCT/US97/14826, filed Aug. 15, 1997; the U.S. patent application Ser. No. 09/001,782, filed on Dec. 31, 1997, now U.S. Pat. No. 6,086,525, which is a continuation-in-part of U.S. patent application Ser. No. 08/345,572, filed Nov. 28, 1994; and the U.S. patent application Ser. No. 09/125,646, filed Mar. 15, 1999, now U.S. Pat. No. 6,132,361, which is a continuation-in-part of U.S. patent application Ser. No. 08/345,572, all the disclosures of which are incorporated herein by reference.

This application is also related to the U.S. non-provisional application Ser. No. 09/501,457 entitled Placebo Seat for Incontinence-Related Magnetic Stimulation Research filed Feb. 10, 2000, the disclosure of which is fully incorporated herein by reference.

FIELD OF THE INVENTION

The invention relates to an apparatus and a method for simulating the sounds and vibrations of a genuine magnetic nerve stimulator, in the preferred version, a transcranial magnetic stimulator ("TMS"), while reducing the induced current for the device from reaching the patient. The present invention relates to a sham TMS which presents the appearance, noise, apparatus, etc. of a genuine TMS, but which, in fact, may be used as a placebo in clinical studies to determine the therapeutic effectiveness of the genuine magnetic nerve stimulator or TMS.

BACKGROUND OF THE INVENTION

TMS is well known in the art. Magnetic stimulation realizes the electric fields necessary for the charge transfer by induction. Magnetic stimulation may be used to induce electric fields in biologic tissue. Rapidly changing magnetic fields induce electric fields in biologic tissue, and when the proper rates, intensity, depth of penetration are achieved, the magnetically induced electric field accomplishes transferring charge directly into the neuron to be excited. TMS involves the magnetic stimulation of neurons in the brain and has been used in the localization, characterization and treatment of brain function. TMS is known to non-invasively alter the function of the cerebral cortex. (See e.g. George M S, Wasserman E M, Post Rm, Transcranial magnetic stimulation: A neuropsychiatric tool for the $21^{st}$ century, *J. Neuropsychiatry*, 1996 8:373-382, the disclosure of which is fully incorporated herein by reference). The magnetic fields used in transcranial magnetic stimulation are generally generated by large, rapidly-changing currents passing through a wire coil on the scalp. Use of a coil with a ferro magnetic core of a material with a saturability of at least 0.5 tesla has been found to be very effective.

Two recent studies have suggested that rapid rate transcranial magnetic stimulation (rTMS) may be used for exploring the functional neuroanatomy of emotions: emotionally healthy volunteers who received left pre-frontal stimulation reported an increase in self-rated sadness, while, in contrast, right pre-frontal stimulation to similarly healthy volunteers caused an increase in happiness. (See, Pascual-Leone A., Catala M D, Pascual A P, Lateralized effect of rapid rate transcranial magnetic stimulation of the prefrontal cortex on mood, *Neurology*, 1996; 46: 499–502; and, George M S, Wasserman E M, Williams W., et al., Changes in mood and hormone levels after rapid-rate transcranial magnetic stimulation of the prefrontal cortex, *J. Neuropsychiatry Clin. Neurosci.* 1996; 8: 172–180, the disclosures of which are also fully incorporated herein by reference.)

Other reports have begun to delineate the therapeutic use of rTMS in depression. The earliest such studies used round, non-focal coils centered at the cranial vertex, with stimulation rates well under 1 Hertz (Hz). Results were promising but not always statistically significant. (See, Hoflich G., Kasper S. Hufnagel A. et al., Application of transcranial magnetic stimulation in treatment of drug-resistant major depression: a report of two cases, *Human Psychopharmacology*, 1993; 8: 361–365; Grisaru N., Yarovslavsky U., Abarbanel J., et al., Transcranial magnetic stimulation in depression and schizophrenia, *Eur. Neuropsychopharmacol.* 1994; 4: 287–288; and, Kilbinger H M, Hofilich G., Hufnagel A., et al., Transcranial magnetic stimulation (TMS) in the treatment of major depression: A pilot study, *Human Psychopharmacology*, 1995; 10: 305–310, the disclosures of which are fully incorporated herein by reference.)

Subsequently, George et al., described a striking improvement in some depressed patients from the treatment with rTMS over the left pre-frontal cortex. (See, George M S, Wasserman E M, Williams W A, et al., Daily repetitive transcranial magnetic stimulation (rTMS) improves mood in depression, *NeuroReport*, 1995; 6: 1853–1856; and, George M S, Wasserman E M, Williams W E, Kimbrell T A, Little J T, Halleft M., Post R M, Daily left prefrontal rTMS improves mood in outpatient depression: a double blind placebo-controlled crossover trial, *Am. J. Psychiatry*, 1997 (in press), the disclosures of which are fully incorporated herein by reference). A large study was reported by Pascual-Leone et al., who used a five-month double blind placebo-controlled cross-over design with five different treatment conditions. (See, Pascual-Leone A., Rubio B., Pallardo F. Catala M D, Rapid-rate transcranial magnetic stimulation of left dorsolateral prefrontal cortex in drug-resistant depression, *The Lancet*, 1996; 348: 233–237, the disclosure of which is fully incorporated herein by reference.) Left pre-frontal rTMS was uniquely effective in 11 of 17 young (less than 60 years of age) psychotically depressed and medication resistant patients.

A recently developed TMS was disclosed by the present applicant and Charles M. Epstein in the PCT International Application NO. PCT/US97/14826, filed Aug. 15, 1997. That disclosure is therefore specifically incorporated herein by reference.

The TMS studies have demonstrated a need for a sham TMS, which may be used as a placebo, to provide a control to determine the effectiveness of a device genuinely providing TMS. There is a need for a sham TMS which can be effectively used in placebo-controlled TMS blind studies. Accordingly, it is a goal of the present invention to provide a sham apparatus for transcranial magnetic stimulation, which may be used in placebo-controlled blind studies to further investigate the uses and effectiveness of TMS in the treatment of patients. Such a sham device must simulate, as much as practicable, the apparatus under investigation, while shielding the induced current of the device from reaching the patient, especially since the studies are related to ephemeral concepts, e.g., self-perception, depression, etc. concepts which are difficult to accurately measure.

SUMMARY OF THE INVENTION

An object of the present invention is to provide an apparatus for imitating the external appearance, sounds and vibration of a genuine TMS while keeping low the induced current which is actually transmitted to the patient.

It is a further object of the present invention to provide a sham TMS which may be used as a placebo in studies to determine the effectiveness of a TMS apparatus and/or procedural protocol under investigation.

A further object of the present invention is to provide a method and an apparatus for realistically simulating a TMS, to be used as a control in legitimate and verifiable medical studies.

As disclosed more fully hereafter, a method and an apparatus is described for realistically simulating a TMS wherein the induced current reaching the patient is kept to a very small percentage of the functioning core which is not provided with the sham shroud. The apparatus placebo comprises the genuine TMS device, modified however, such that an aluminum shroud is situated over the core's end faces. The aluminum plate absorbs a significant amount of the transmitted energy from the TMS, thus substantially keeping the induced current from penetrating to the patient who is receiving the TMS placebo treatment and/or device.

BRIEF DESCRIPTION OF THE DRAWINGS

The apparatus of the present invention will now be described with reference to the accompanying drawing figures, in which.

DETAILED DESCRIPTION OF THE PREFERRED EMBODIMENTS

The design of the invention is related to the design for a functioning or operational TMS as previously described in U.S. patent application Ser. No. 08/345,572 filed Nov. 28, 1994 (the continuation of which is pending) and in PCT International Application No. PCT/US97/14826, filed Aug. 15, 1997, the disclosures of which are all fully incorporated herein by reference. Also incorporated by reference is U.S. Pat. No. 5,725,471, issued to Neotonus, Inc. which describes a preferred form of a magnetic nerve stimulator. Drawings relating to operational magnetic stimulators are provided in FIGS. 1 through 4. The specifications and details of the components of an operational stimulator are set forth in the PCT International Application No. PCT/US97/14826, filed Aug. 15, 1997 and in U.S. Pat. No. 5,725,471.

Figure 1:
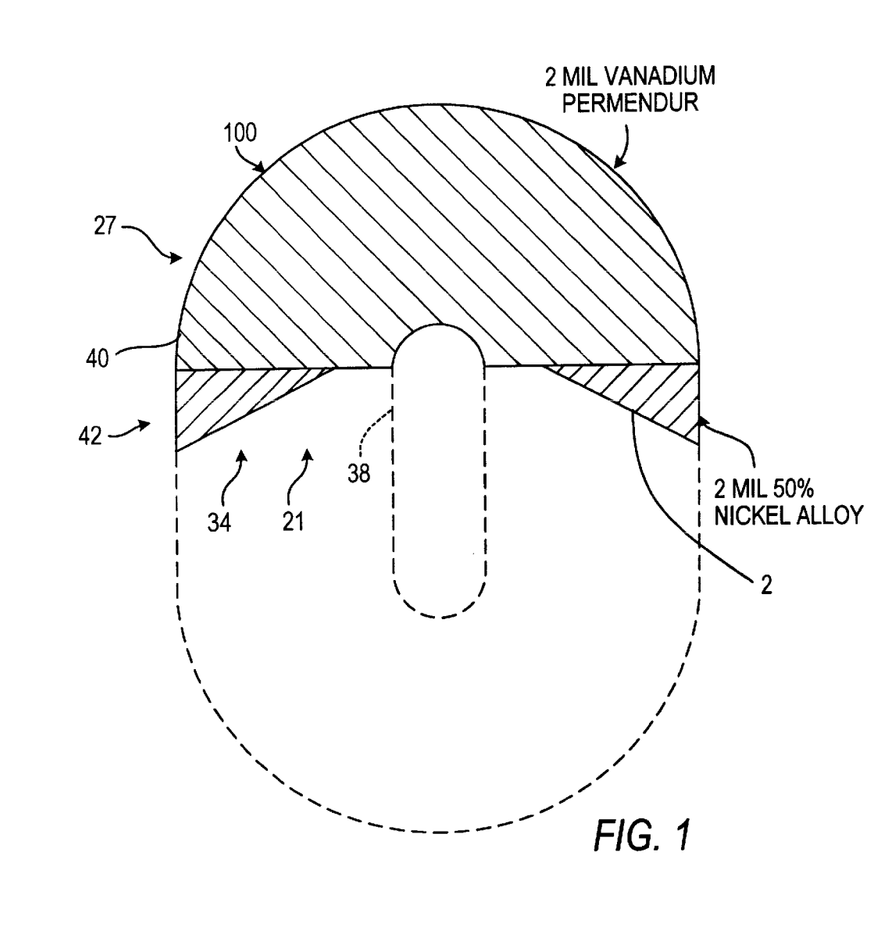
FIG. 1 is a side view of a core segment of a transcranial magnetic brain stimulator, shown without the aluminum shroud of the present invention.
Figure 4:
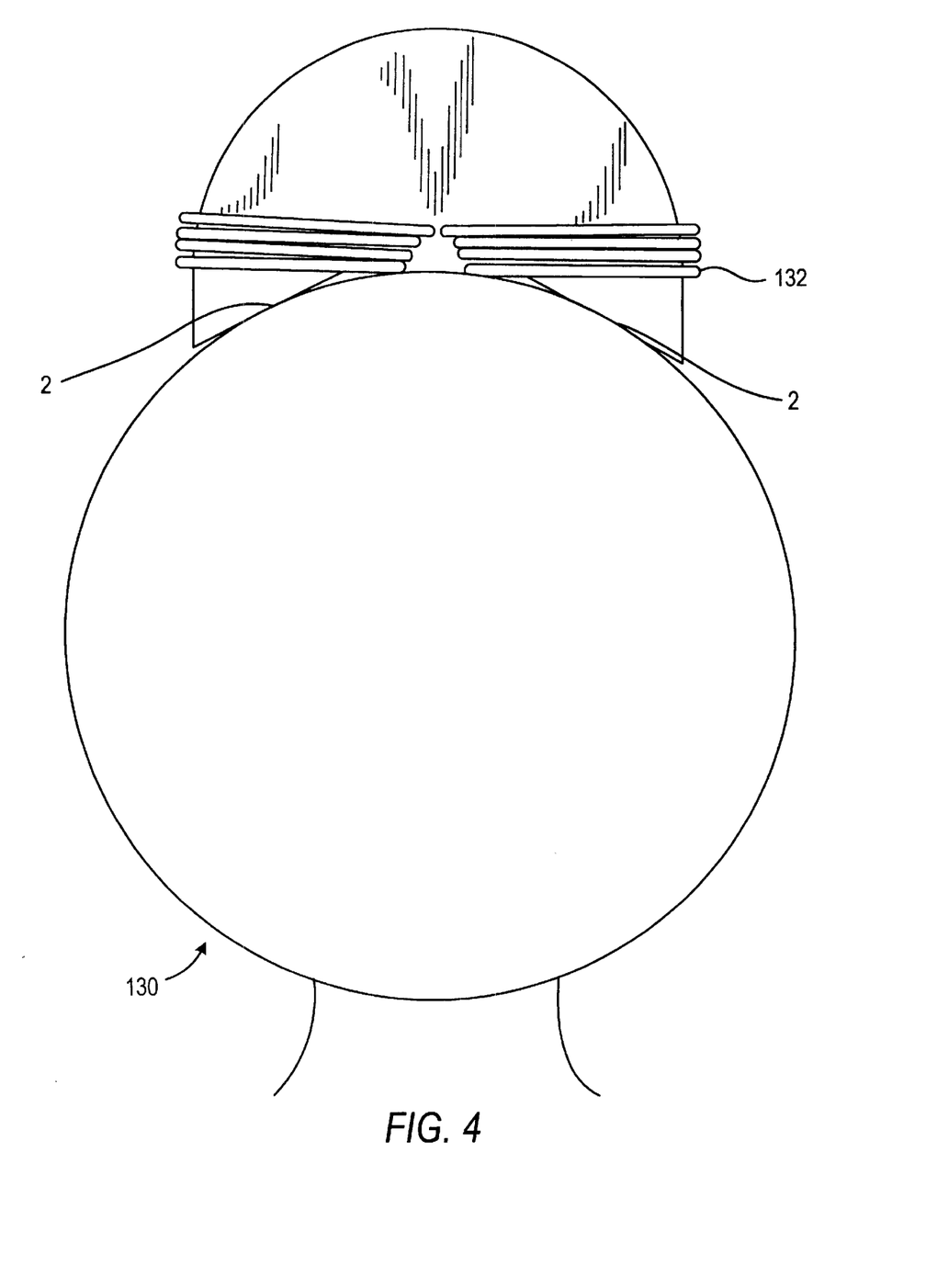
FIG. 4 is a side view of the transcranial magnetic brain stimulator shown in FIG. 3, without the aluminum shroud of the present invention, again shown placed on a schematic human head.

In one operational magnetic nerve stimulator, the stimulator may induce electric fields similar in distribution to those from a Cadwell water-cooled figure-eight coil. As shown in FIG. 1, in an operational magnetic stimulator, a core (27) for the magnetic nerve stimulator is provided for stimulation of the brain. The stimulator core 27 is made of a magnetic material, preferably a ferromagnetic material. The stimulator core segment is basically hemispherical and terminates with two rectangular end faces (2), as shown in FIG. 4 Preferred materials for the core of an operational magnetic stimulator include vanadium permendur or 3% grain oriented steel.

As shown in FIG. 1, an example of the core of an operational magnetic stimulator, core segment 27 is cut from an oval winding of 2 mil vanadium permendur. Two core segments can, in fact, be cut from a single oval winding, by cutting one core from each side of the oval. For illustration purposes, only a single core segment is shown in the diagram of FIG. 1.

A method of construction of such a core is as described previously in the patent application, which is related to the present application, U.S. application Ser. No. 08/345,572, filed Nov. 28, 1994 and the continuation thereof. Cores may be constructed from thin laminate, highly saturable material (i.e. materials with a saturability of at least 1.5–2.0 Tesla, although less saturable materials with a saturability of 0.5 Tesla and higher can be used as well). A typical core can be made by winding two mil stock of vanadium permendur. A long ribbon of such material is wound on a mandrel (e.g. a mandrel of wood or plastic) for the radius, thickness and depth desired. Each side of the ribbon is coated with a thin insulative coating to electrically isolate it from its neighbor. After cutting the core segment 27 from the entire oval winding, a suitable core might span a preferred angle of approximately 208°, or in the range of about 205–215°. Other angles are possible, as well. Once the ribbon has been wound on the mandrel to the desired dimensions, it is dipped in epoxy to freeze its position. Once the epoxy has dried, the mandrel is removed and the core segments may be cut for the span of angle desired. The cut may destroy the electrical isolation of adjacent laminations. Each cut foil then must be finely ground so that it is smooth, and then a deep etch is performed. The deep etch is performed by dipping each of the cut ends in an acid bath. This causes the cut ends to slightly delaminate, but maintains the electrical isolation of the laminations. Failure to perform this deep etch seems to result in considerable eddy current loss and heating at the cut ends of the core segments. Following the deep etch, the ends are brushed with epoxy to maintain the shape and structural integrity of the core segment. The final step of the construction of an operational magnetic stimulator is to wind a coil of insulated wire about the one or more, side by side core segments. A typical inductance for a core of this type is about 20 μH. The operational magnetic stimulators however, may be practiced at other inductances or magnetic field strengths, if desired.

Figure 2:
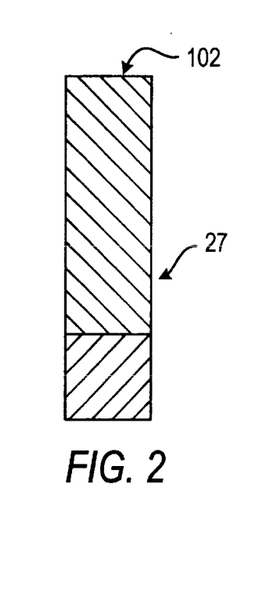
FIG. 2 is a front view of a core segment of the transcranial magnetic brain stimulator shown in FIG. 1, again without the aluminum shroud of the present invention.

As an alternative to cutting the core segment as a single section, the core can be first cut into a semi-circular section. In this method of manufacture, small triangular sections or wedges 34 at the bottom of the core are then cut separately, and attached to the semi-circular section as shown in FIG. 1. The smaller triangles may also be made from vanadium permendur. If necessary, however, the triangles can be any material or alloy that has a saturation of at least 0.5 Tesla. A suitable alloy for the triangular wedge sections, for example, is 2 mil 50% nickel alloy. As shown in FIG. 1, in one example of the core for an operational transcranial magnetic stimulator, core 27 has an outer diameter of approximately 4.75 inches. The core 27 has an inner semicircular aperture at the center of the core segment 27. Inner semicircle aperture has a diameter of approximately 0.75 inches. In the version where the smaller triangles are separate, triangular sections or wedges 34 are attached to the larger semi-circular section. Triangular sections 34 have a length on longer side (with respect to the shorter leg, not the hypotaenuse), in contact with semi-circular section 30, of approximately 1.375 inches, and a length of approximately 0.75 inches on shorter side 42 which is approximately coplanar with the outside circumferential wall of the semi-circular section. As shown in FIG. 2, the cross sectional width of core segment 27 is approximately 0.625 inches and the wedges 34 are about the same thickness. As shown in FIG. 1, each of the core segments of the operational stimulator may be an open core, i.e. the core forms an open arc and does not constitute a closed toroid. An approximately C-shaped or horseshoe core is preferable. At least a portion of the core of the stimulator conforms, at least approximately, to the shape of the head. A hemispherical stimulator, having at least one, but preferably four adjacent, core segments (see FIG. 3) made of saturable or highly saturable ferromagnetic material may be used. The span of the core affects both the penetration depth of the magnetic field and the magnitude of the field. While a variety of angles are acceptable for the curvature of the arc of the core, a core of 208 degrees or approximately in the range of about 205–215 degrees (as shown in FIG. 1) is preferred and desired. Cores of approximately 190–230 degrees can be utilized. Alternatively, a core spanning an arc of approximately 180–270 degrees is also possible, although not necessarily believed as effective.

Figure 3:
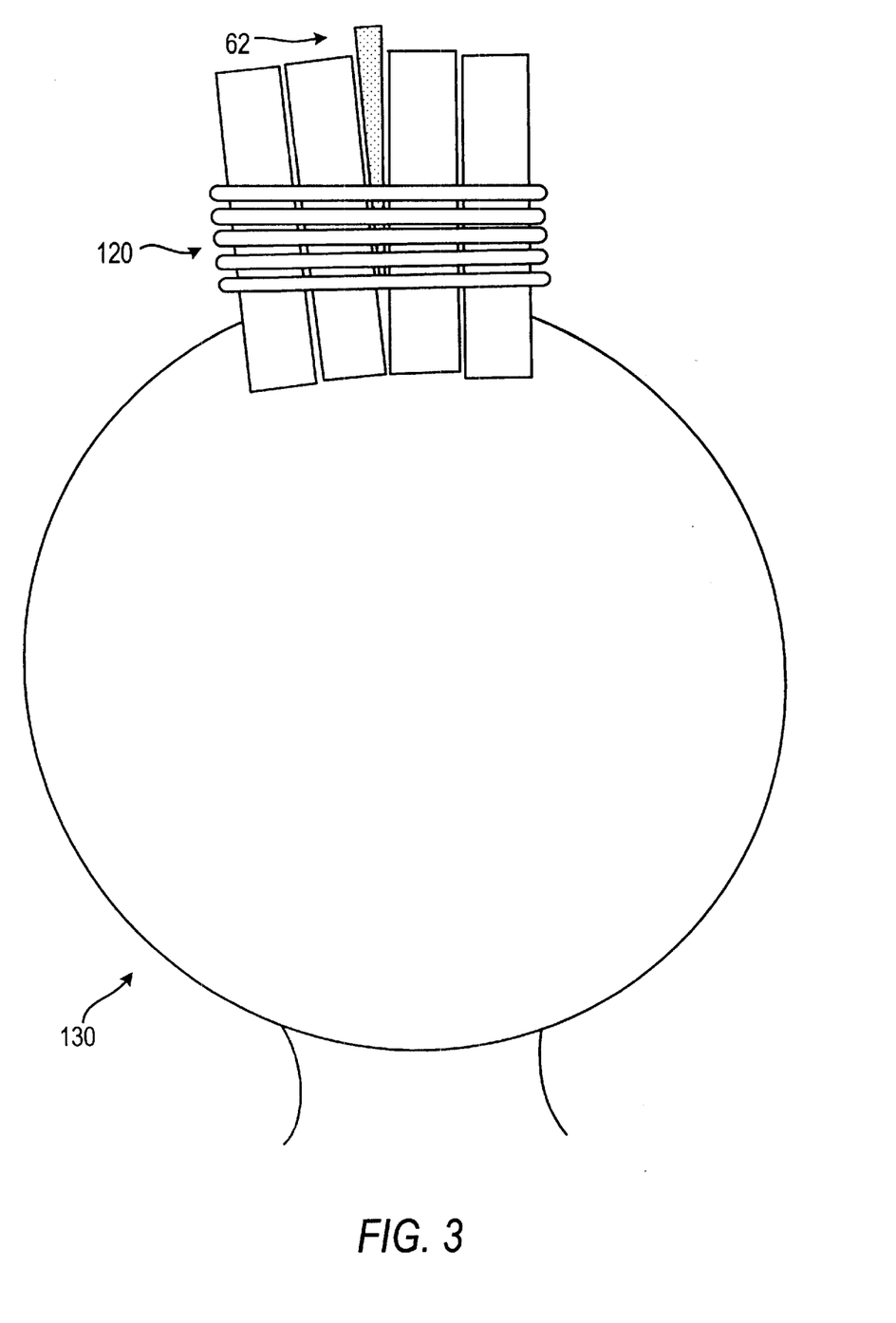
FIG. 3 is a front view of a transcranial magnetic brain stimulator, formed from four cores of the type shown in FIGS. 1 and 2, again without the aluminum shroud of the present invention, with a port between the middle core segments, a positioner in the locating port, and a coil schematically wrapped around the core segments, as positioned on a schematic human head.

To form an operational stimulator, four core segments may be positioned approximately flat side by flat side to form a complete magnetic stimulator. Although more than four core segments or less than four core segments are possible, four are preferred. As shown in FIGS. 3 and 4, two pairs of cores are placed side by side to form, by their open ends, a hemisphere-like opening designed for placement on a section of the head. The combined core segments are wound with a series of windings of wire to form a single functioning core component. Approximately nine to ten turns of wire may be used. In practice, it has been found that approximately nine (9) turns of wire should be wound around the larger stimulator formed of a single core segment of FIG. 1, and approximately ten (10) turns of wire should be wound around the stimulator formed of several core segments. As shown in FIGS. 3 and 4, approximately four–five (4–5) turns of wires are wound around each half of the stimulator, i.e., approximately four to five turns are wound around a first side or leg of the stimulator, and another four to five turns are wound around the second side or leg of the stimulator. The stimulator may be provided with a visualization and location port passing from outside circumferential wall to the inside for viewing and marking the head and locating and precisely relocating the stimulator thereon. A space is left open between the two pairs of cores to form a center port 62 (see FIG. 3). Center port 62 extends from the top of the stimulator down to the surface of the patient's head as shown in FIG. 3. A length of plastic or copper tubing may be inserted in this area to form the port. Port 62 is of a sufficiently large diameter that a marking device such as a pen or felt marker can be inserted into the port 62 through the stimulator to initially mark the head's surface (or to mark a cap worn on the head). This marking facilitates repositioning on the same spot of the patients head. Thus, as an illustration of the construction and use of the port 62, the internal ink containing cylinder can be removed from a standard writing device, such as a Papermate™ pen, leaving the pen's outer plastic section of tubing empty. This outer plastic section of tubing can be inserted between the two pairs of cores to serve as the tubing for the port. The internal, ink containing portion of the pen, can later be inserted down and through this port to mark the patient's head or the worn cap. Any suitable tubing and any marker of smaller diameter than the tubing, can of course, be used. Port 62 has importance both as a means to precisely mark where a stimulator is located on the head, and as a means to precisely position the stimulator. When the stimulator is placed on the head, the marking device or pen can be inserted down the port 62 and through the stimulator to make a mark on the head of the patient. The mark serves as an effective reference, indicating exactly where the stimulator was positioned. This provides a convenient and effective means of precisely recording the stimulator location for later reference. Likewise, if it is desired that the stimulator be centered over a particular region of the head, a mark can first be placed on the head in the appropriate area and the stimulator adjusted so that the port overlays (determined by visualization) the marked location. Or, if it is desired that the stimulator be placed on the same location in successive sessions, an appropriate mark can be left on the head or cap after the first positioning. In either situation, by viewing down the port of the stimulator, the stimulator can be moved around over the head until the marked area is within view through the open port, so that the stimulator can be positioned on the exact location desired.

The electrical circuitry employed with an operational stimulator is well known in the art. Reference is also made to the co-pending application Ser. No. 08/345,572 filed Nov. 28, 1994 and any continuation application for the operational stimulator taught therein and to the U.S. Pat. No. 5,725,471, the disclosures of which are incorporated by reference. Thus, in the design of an operational TMS, as shown in FIG. 1, the semi-circular configuration combines with a double-loop wire coil, and the concave or basically hemispherical active surface delivers magnetic flux to the brain and other physiological targets.

Figure 5:
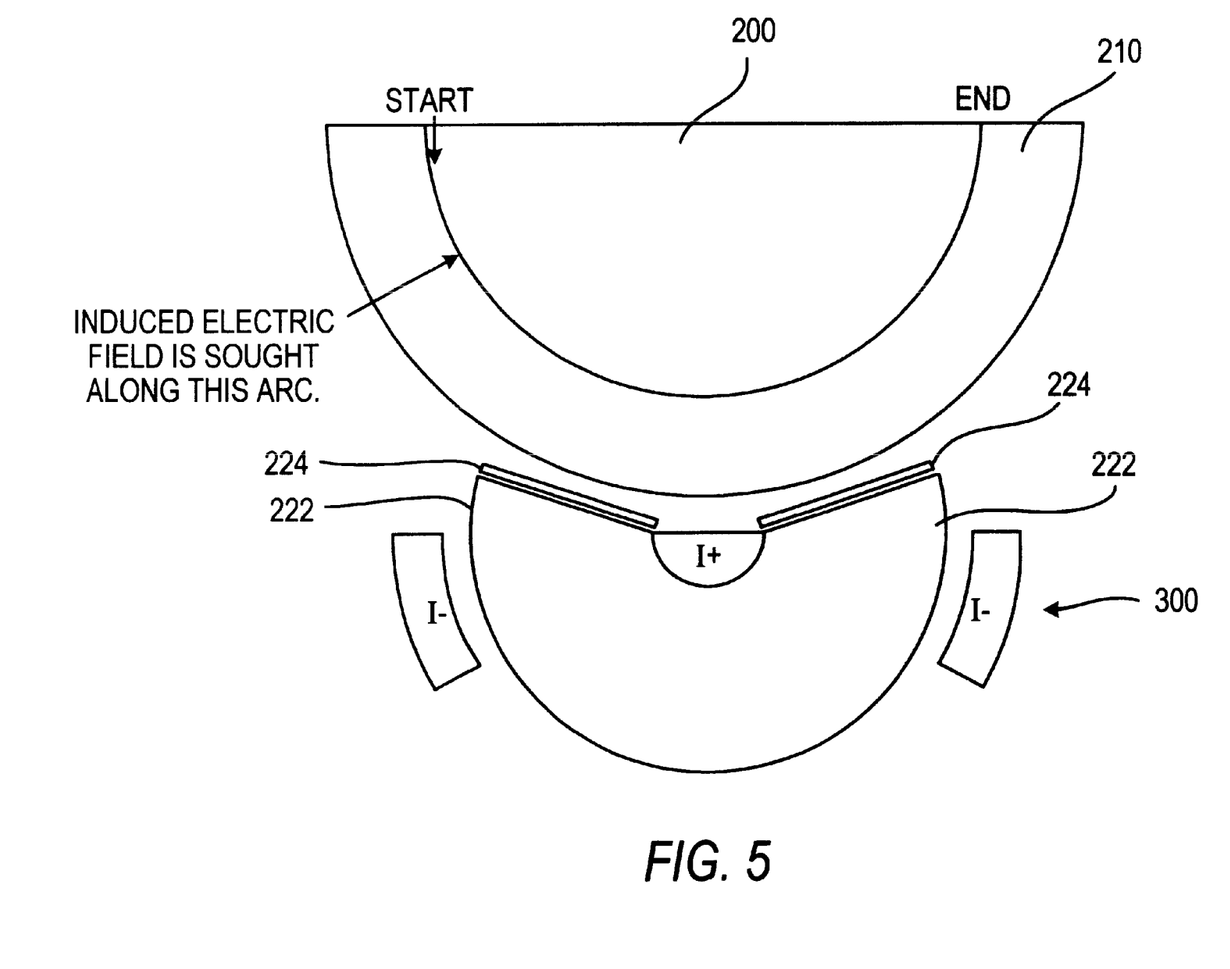
FIG. 5 is a schematic side view of a TMS, equipped with a pair of 1/16 inch thickness aluminum plates over the end faces of a core of the type shown in FIGS. 1–4, in conjunction with a saline tank, representative of a human head, to determine the effect of the sham, i.e., the manner that the plates effect the penetration/transmission of magnetic flux.

Turning attention to FIG. 5, the present invention involves a sham transcranial magnetic stimulator (300), comprising a transcranial magnetic stimulator, having a ferro magnetic core (220) made of one or more core segments, wherein the core has a pair of exposed core or end faces (222) (rectangular in cross section); and a metal shroud, preferably aluminum (224) is placed over each of the core end faces (222). The core induces an electric field. The sham device includes the metal shroud, preferably aluminum (224), and it is placed over the end faces of the core poles or end faces (222). The shroud absorbs energy emitted from the stimulator. Thus, the placement of a metal shroud (224) preferably aluminum, over the faces of the core poles (222) of an otherwise fully operational TMS results in a sham TMS, which otherwise imitates the sound, vibration and external appearance of a functional or operational TMS, but the aluminum shroud protects the patient from the induced electric field generated by the functioning core (220) of the TMS. The sham transcranial magnetic stimulator comprises a transcranial magnetic stimulator of the type known in the art to be fully functional and having a ferro magnetic core, wherein the core has two end faces; and a continuous metal shroud is placed to extend contiguously over and preferably extending across the two faces of the core. The sham TMS allows the genuine TMS to be used in scientific research. The sham, then, is the equivalent of a placebo. Use of the metal shroud on the ends of the core minimizes the magnetic flux generated by the device from penetrating the body since the flux barely penetrates through the aluminum plate. A saline tank has been used to show the effectiveness of the shroud.

Three different embodiments are described herein for an aluminum shroud over the core poles or end faces (222). However the invention is not limited to the specific embodiments set forth in this application.

Figure 8:
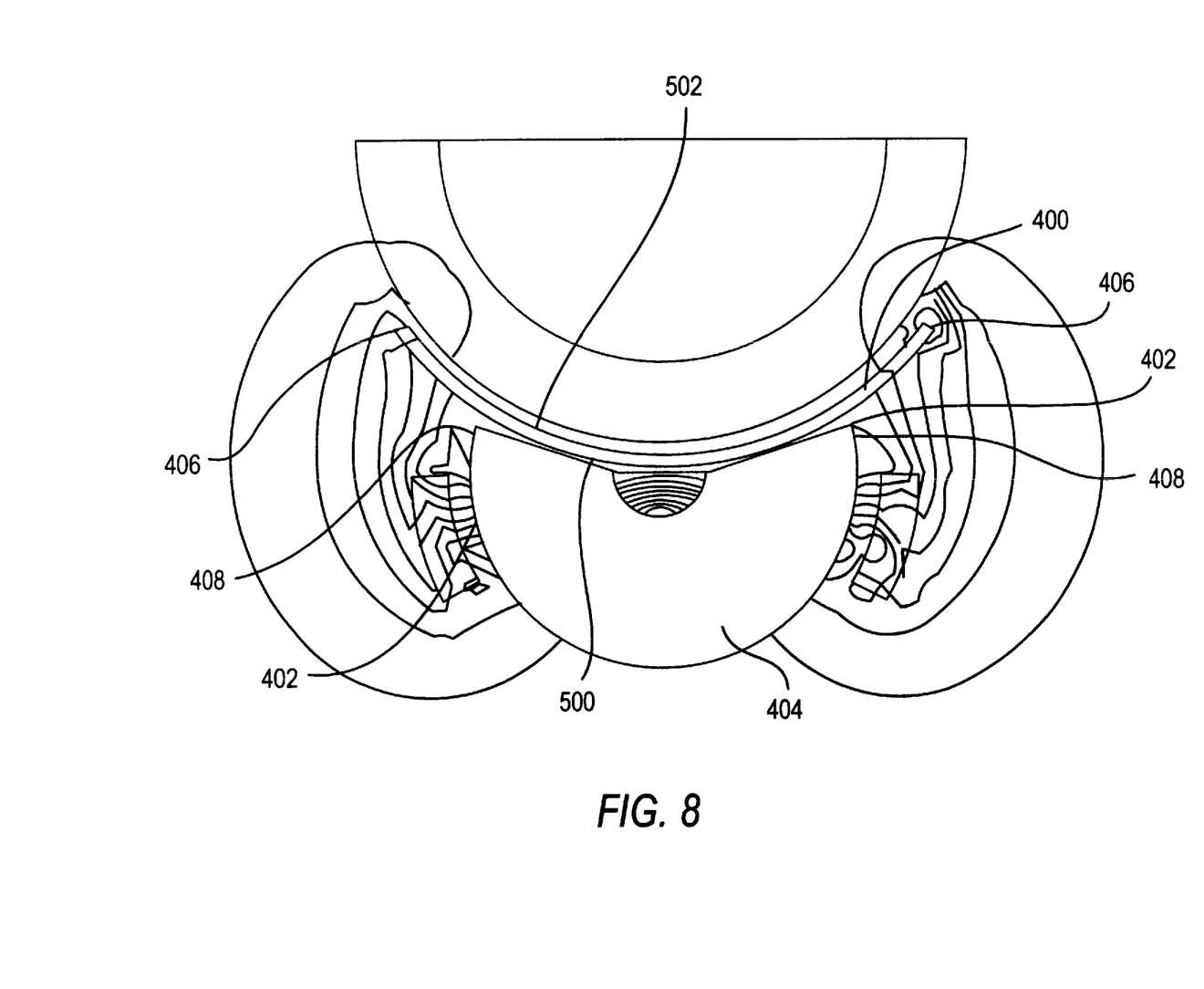
FIG. 8 is a view similar to that of FIGS. 5 and 6, showing a 110 degree arc formed by a 1/8 inch aluminum plate as a sham.

The preferred embodiment of the shroud is an approximately ⅛" aluminum plate, bowl-shaped shroud (400) that has a significantly wider reach than the extension of the core faces (402) themselves, as shown in FIG. 8. In a preferred embodiment, the approximately ⅛" bowl-shaped shroud (400) is an aluminum plate spanning approximately 110 degrees with a mean radius of approximately 3.1375 inches and the bowl shroud (400) is placed over the core faces (402), as shown in FIG. 8. The core (404) may be made as previously described and may have a C-shape or horseshoe shape with its two rectangular end faces (402) directed toward yet superimposed by the bowl-shaped shroud (400).

The sham transcranial magnetic stimulator of the present invention simulates the sounds and vibration of the real TMS unit, but keeps the induced current reaching the patient down to a very small percentage of a fully functioning TMS. The use of a shroud with an otherwise functioning TMS, protects the patient from the electric field induced by the core of the TMS. Placing an aluminum shroud over the core or end faces protects the patient from much of the flux and shields the patient from the induced electric field. The aluminum shroud is placeable on or near or directed toward the appropriate part of the body during the sham procedure. In transcranial magnetic stimulation, the TMS is placed on the head of the patient. In a sham transcranial magnetic stimulation placebo treatment, the sham TMS is similarly situated on the head of the patient, whereby the shroud shields the patient from the induced electric field. Thus, a double blind scientific study seeking to show the effectiveness of the TMS can be performed.

The thickness and the length of extension of the shroud determine the effectiveness of the shroud in shielding the patient from the induced electric field. Experimentation with different thicknesses and angular extensions of the shroud has been done. For purposes of the experiments, a saline water tank (200) was utilized to mimic a patient's head, as shown schematically in FIG. 5.

Figure 6:
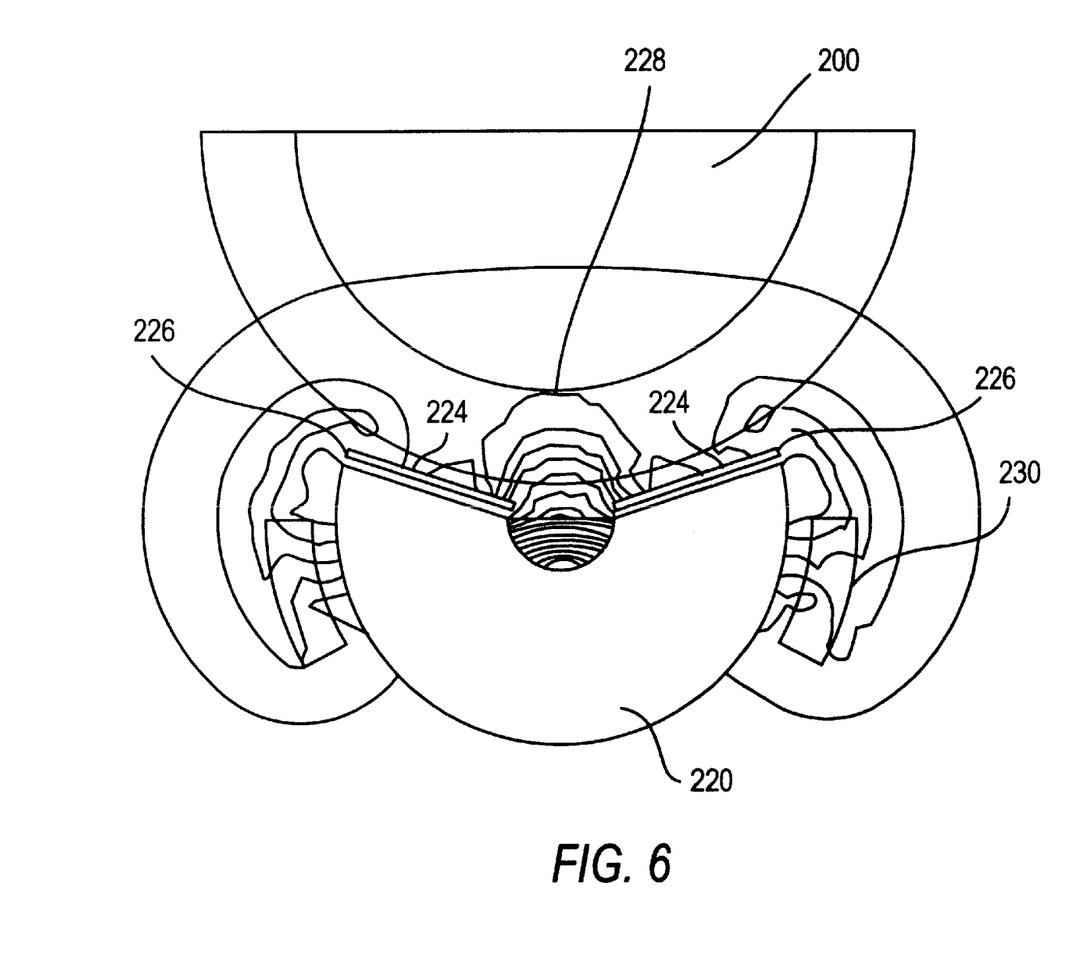
FIG. 6 is a view similar to that of FIG. 5, showing a field plot of the base sham TMS of FIG. 5 showing field concentration at the edges of the plates.

Shown in FIG. 5 is the geometry of a simple sham, using a pair of 1/16" rectangular aluminum plates (224) just covering the end faces of the core (220). The target arc for purposes of determining the effectiveness of the sham, (210) is located 2 cm interior to the bowl i.e., within the saline tank. The TMS is excited to 24,500 AT at 3567 Hz. The investigation concerned how well this configuration prevented field penetration to the saline tank. Shown in FIG. 6 is the field plot of the basic sham plates of FIG. 5, showing the field concentration (230) near the edges (226) of the plates. The center and the edges show field penetration into the hoped-for protected target region (228). This degree of penetration is believed undesirable. A redistribution of the field also results from the plates, resulting in rather significant induced E fields further out along the arc (near 3:00 and 9:00 if the view were considered a clock face). A field comparison makes this clear.

Figure 7:
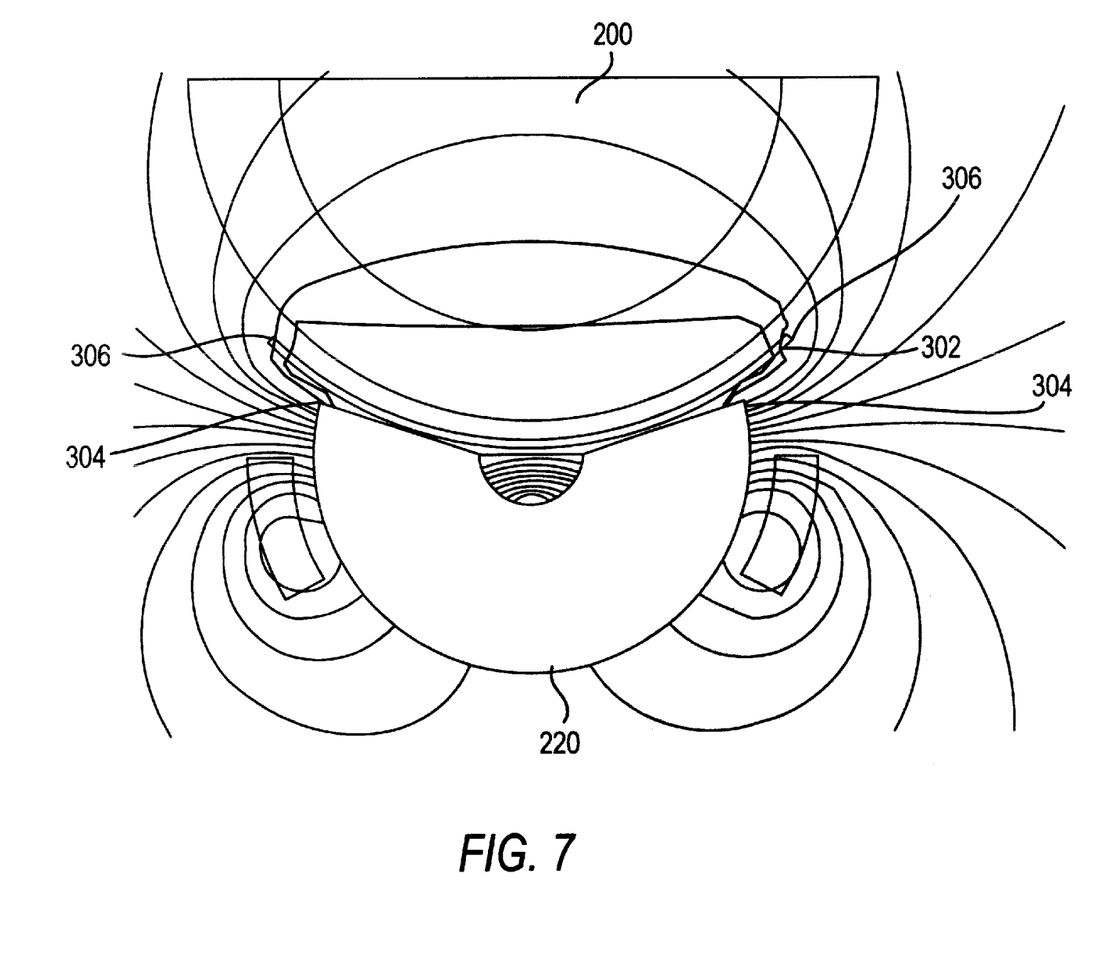
FIG. 7 is a view similar to that of FIGS. 5 and 6, with a 1/16 inch aluminum arc-shaped sham spanning 90 mechanical degrees i.e., the aluminum plate extends from –45 to –135 degrees.

A second embodiment is shown in FIG. 7 wherein the isolated plates of FIG. 6 are replaced with a continuous 1/16" aluminum arc (302) covering the angle from about −45 to −135 degrees. Thus, the aluminum arc (302) spans about 90 mechanical degrees, covers the core's end faces and extends through the center of the core, and the edges (306) of the aluminum arc (302) extend past the edges (304) of the core (220). The full arc prevents much of the field leakage up the center. Much of the field is still, however, cutting across the tips of the 90° arc sham.

As a preferred embodiment of the sham plate design, the aluminum plate was thickened to 0.125" or ⅛ inch and the continuous arc was further increased from 90° to about 110°, as shown in FIG. 8. Thus, in the preferred embodiment, the ⅛ inch continuous aluminum plate spans about 110 degrees with a mean radius of 3.1375 inch. The ⅛" aluminum plate (400) covers the core (404), the center of the core, and the edges of the aluminum plate (406) extend well beyond the edges or ends (408) of each of the two core faces (402). The aluminum plate (400) has an upper or concave side (502) and a lower or convex side (500). The field is more effectively contained to the lower side (500) of the arc-shaped sham plate. As with FIG. 7, in FIG. 8, some field penetration still occurs near the outer tips of the plate. Thus, the ⅛ inch continuous aluminum plate, spanning 110 degrees, more effectively directs the field away from the target region. In this third and preferred embodiment, the sham transcranial magnetic stimulator, comprises a transcranial magnetic stimulator, having a ferro magnetic core of a basic C-shape, wherein the core has two rectangular end faces and a continuous aluminum sheet shroud is placed to extend across the two end faces and center of the core and said aluminum shroud extends past the ends of each of said faces of the core.

Figure 9:
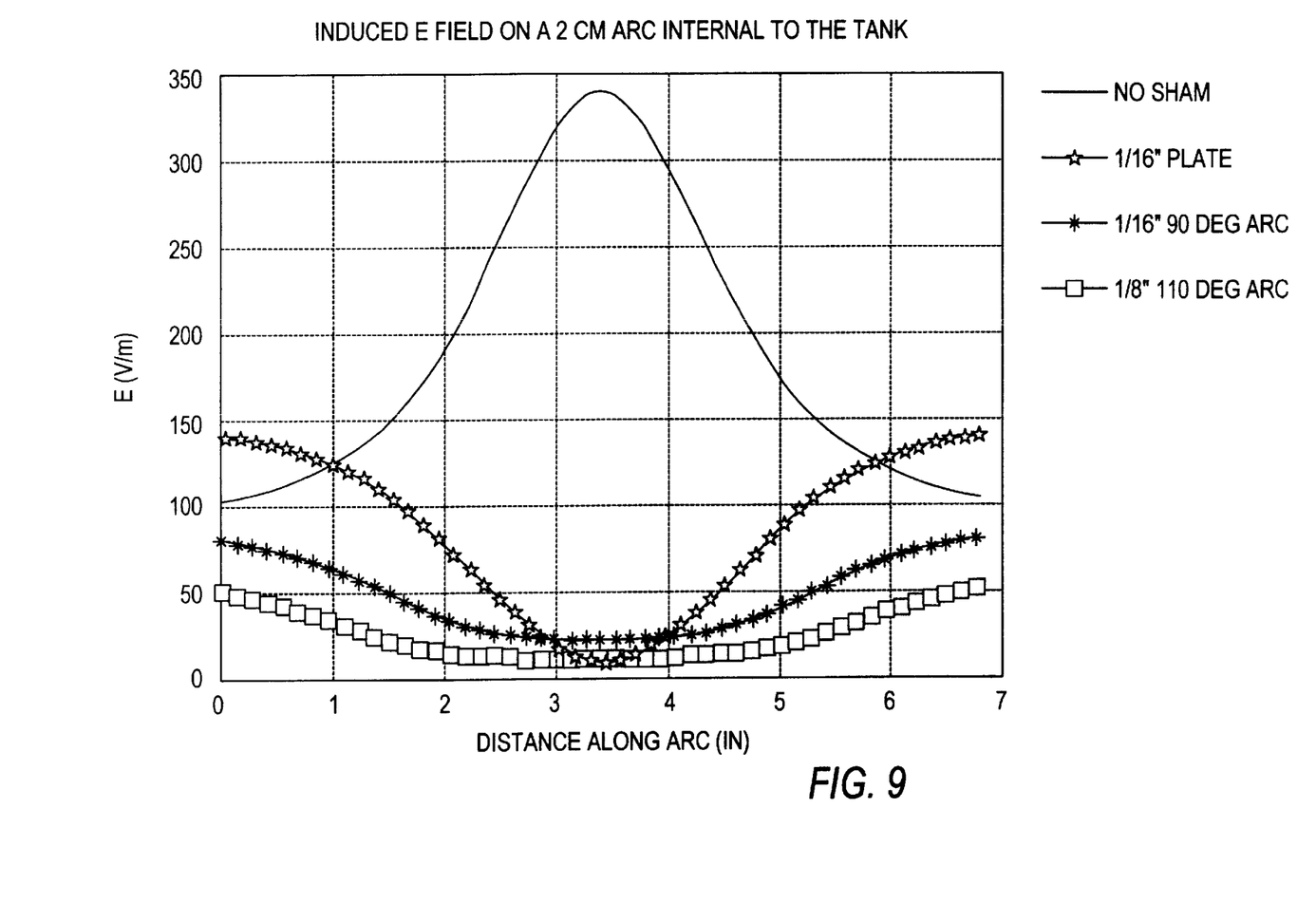
FIG. 9 is a chart of the Induced E field for no sham; the 1/16" aluminum plate sham; 1/16" continuous aluminum plate spanning 90° arc; and 1/8" continuous aluminum plate sham, spanning a 110° arc within the saline tank, as a function of distance (in inches) along the arc.

A quantitative graph of the induced E field along the arc (210) shown in FIG. 5 is the best way to discern the effectiveness of these alternative sham devices. The induced E field is predicted along the complete arc. FIG. 9 shows the induced E field in situations where there is: 1) No sham; 2) 1/16" aluminum end plates; 3) 1/16" continuous aluminum end plate of 90 degree arc and 4) ⅛" continuous aluminum plate of 110 degree arc. For the no sham case, the E field peaks at the center of the core of FIG. 5, whereas it peaks near the core ends of the arc when the aluminum plates are present. This is due to the plates driving the flux outward of the aluminum plates. The simple 1/16" rectangular end plates only succeed in reducing the maximum E field by a little over 50%. The thicker ⅛" continuous aluminum 110 degree arc sham has a peak induced E field 1/7th of the peak from the original device and near the center it is 1/30th of the induced E field of the original TMS. The ⅛" continuous aluminum 110° plate is most effective in shielding from the center of the core, extending to a distance along the arc. Therefore, in the present invention, the preferred embodiment is where the sham TMS stimulator is constructed by using the ⅛" thick continuous aluminum sheet, of about 110° arc, i.e., the design of FIG. 8. The mean radius of the arc is 3.1375", and the arc spans a minimum of about 110°. In the preferred embodiment, a TMS with sham shroud is covered with thin rubber so that its physical appearance is substantially the same as the TMS without the shroud. It is also preferred that the device be driven at 50% power. Driving the device at full power at 10 Hz with a 50% duty cycle continuously results in 40W of power being deposited in to the sham plate.

Thus, in use, the sham transcranial magnetic stimulator is placed on the head of a patient, the power supply is turned on, the core induces an electric field, and the shroud effectively shields the head of the patient from the induced electric field. The power supply is turned-off after being applied for the time period set in the test protocol. Thus, the sham transcranial magnetic stimulator mimics the external appearance, sound and vibration of an operational transcranial magnetic stimulator and thus, may be used as a placebo in clinical trials to determine the effectiveness of a genuine transcranial magnetic stimulator in various treatments.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A sham transcranial magnetic stimulator for simulating a transcranial magnetic stimulator, comprising:
    a) a transcranial magnetic stimulator, comprising a ferro magnetic core, wherein the core has at least one core end face; and
    b) a metal shroud covering at least a portion of said core end face,
    wherein said metal shroud is located between the patient and said core end face and substantially prevents the magnetic field from reaching the brain of the patient disposed below said sham transcranial magnetic stimulator.

2. A sham transcranial magnetic stimulator, as claimed in claim 1, wherein said core is in the general shape of a horseshoe and said metal shroud is aluminum.

3. A sham transcranial magnetic stimulator, as claimed in claim 1, wherein said shroud comprises rectangular plates which overlay said end faces.

4. A sham transcranial magnetic stimulator, as claimed in claim 1, wherein said shroud is aluminum.

5. A sham transcranial magnetic stimulator, as claimed in claim 1, wherein said shroud is at least 1/16" thick.

6. A sham transcranial magnetic stimulator for simulating a transcranial magnetic stimulator, comprising:
    a) a transcranial magnetic stimulator, having a ferromagnetic core, wherein the core has two end faces; and
    b) a continuous aluminum shroud extending over said center and end faces of the core,
    wherein said metal shroud is located between the patient and said core end faces and substantially prevents the magnetic field from reaching the brain of the patient disposed below said sham transcranial magnetic stimulator.

7. A sham transcranial magnetic stimulator as claimed in claim 6 wherein said shroud extends outwardly beyond the edges of each of said end faces of said core.

8. A sham transcranial magnetic stimulator, as claimed in claim 6, wherein said aluminum shroud is approximately 1/8 inch thick.

9. A sham transcranial magnetic stimulator, as claimed in claim 7, wherein said aluminum shroud spans approximately 110 degrees.

10. A sham transcranial magnetic stimulator, as claimed in claim 6, wherein said transcranial magnetic stimulator is sized to be placed on the head of a patient, and said shroud shields the head of the patient from the induced electric field.

11. A sham transcranial magnetic stimulator, as claimed in claim 6, wherein said aluminum shroud extends at least 90°.

12. A sham transcranial magnetic stimulator, as claimed in claim 6, wherein said aluminum shroud is at least 1/16" thick.

13. A sham transcranial magnetic stimulator, as claimed in claim 12, wherein said aluminum shroud extends at least 90°.

14. A sham transcranial magnetic stimulator, as claimed in claim 9, wherein said aluminum shroud is at least 1/16" thick.

15. A sham transcranial magnetic stimulator, as claimed in claim 1, wherein said aluminum shroud is at least 1/8" thick.

* * * * *